United States Patent [19]

Cottenceau et al.

[11] Patent Number: 5,484,424
[45] Date of Patent: Jan. 16, 1996

[54] BLOOD FILTERING DEVICE HAVING A CATHETER WITH LONGITUDINALLY VARIABLE RIGIDITY

[75] Inventors: Jean-Philippe Cottenceau, Anthony; Gérard Chevillon, Montrouge, both of France

[73] Assignee: Celsa L.G. (Societe Anonyme), Chasseneuil, France

[21] Appl. No.: 152,361

[22] Filed: Nov. 16, 1993

[30] Foreign Application Priority Data

Nov. 19, 1992 [FR] France .................. 92 13909

[51] Int. Cl.$^6$ ............................................. A61M 25/00
[52] U.S. Cl. ............................................. 604/282; 606/200
[58] Field of Search ............................. 604/104, 264, 604/280, 282; 606/191, 198, 200

[56] References Cited

U.S. PATENT DOCUMENTS

| | | | |
|---|---|---|---|
| 4,425,908 | 1/1984 | Simon | 606/200 X |
| 4,673,394 | 6/1987 | Fenton, Jr. et al. | 604/175 |
| 4,781,685 | 11/1988 | Lehmann et al. | |
| 4,983,169 | 1/1991 | Furukawa | 604/164 |
| 5,004,456 | 4/1991 | Botterbusch et al. | 604/53 |
| 5,085,649 | 2/1992 | Flynn | 604/282 |
| 5,152,777 | 10/1992 | Golberg et al. | 606/200 |
| 5,178,158 | 1/1993 | de Toledo | 128/772 |
| 5,234,458 | 8/1993 | Metais | 606/191 X |
| 5,300,086 | 4/1994 | Gory et al. | |
| 5,308,342 | 5/1994 | Sepetka et al. | 604/282 |
| 5,329,942 | 7/1994 | Gunther et al. | 606/200 X |

FOREIGN PATENT DOCUMENTS

| | | | |
|---|---|---|---|
| 0448886 | 10/1991 | European Pat. Off. | |
| 2580504 | 10/1986 | France | |
| 2643250 | 8/1990 | France | |
| 2918282 | 11/1980 | Germany | 604/282 |
| 3203410 | 11/1982 | Germany | |
| 4137132 | 5/1993 | Germany | 604/282 |

Primary Examiner—Corrine M. Maglione
Attorney, Agent, or Firm—Rothwell, Figg, Ernst & Kurz

[57] ABSTRACT

The invention relates to a blood filtration device which can be implanted in a patient's body and comprises a catheter and a blood filter secured to one end thereof. The catheter has a longitudinally variable rigidity, being stiffer at its end where the filter is secured thereto and more flexible at the opposite end where the catheter can be connected to an implantable chamber adapted for distributing a drug in the patient's body.

8 Claims, 4 Drawing Sheets

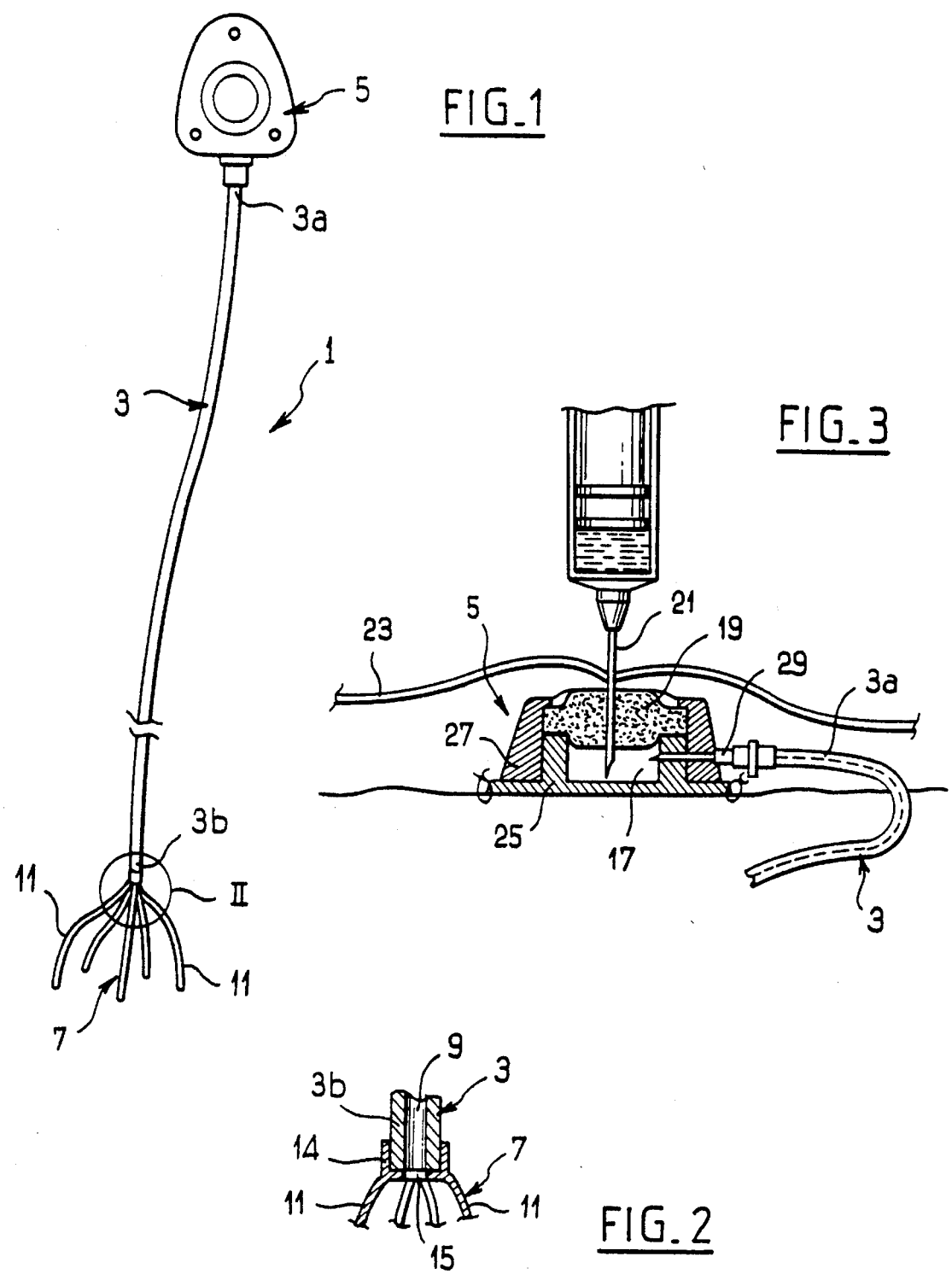

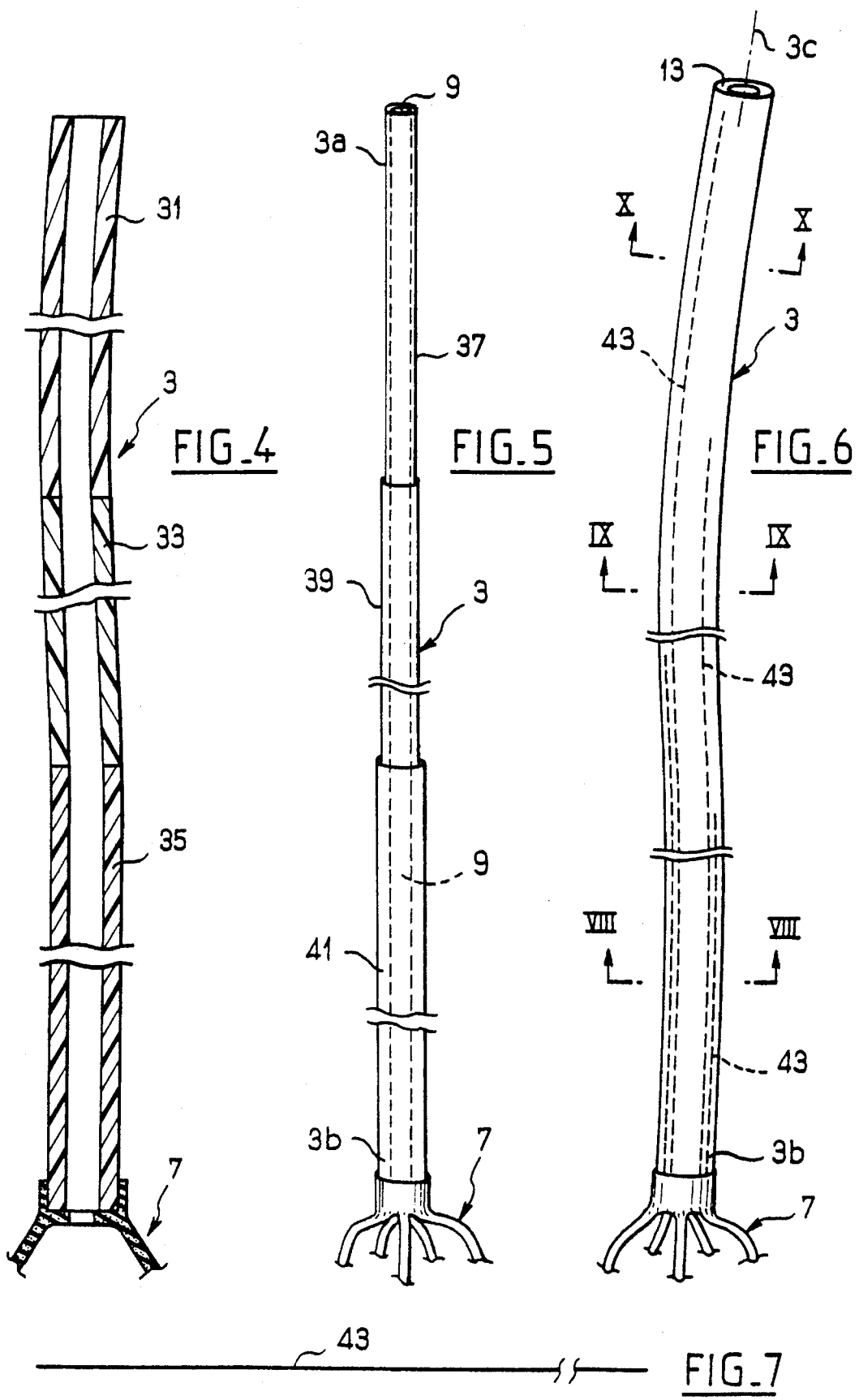

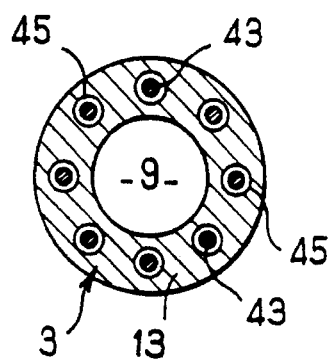
FIG_8
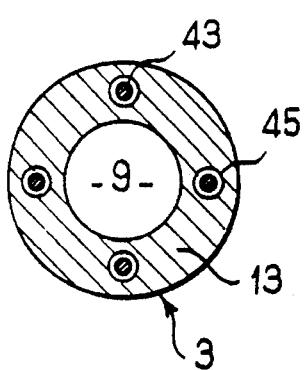
FIG_9
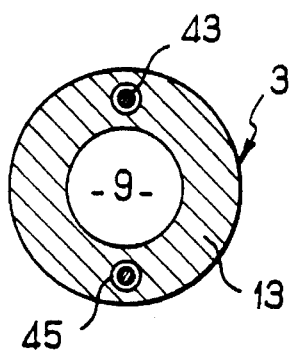
FIG_10
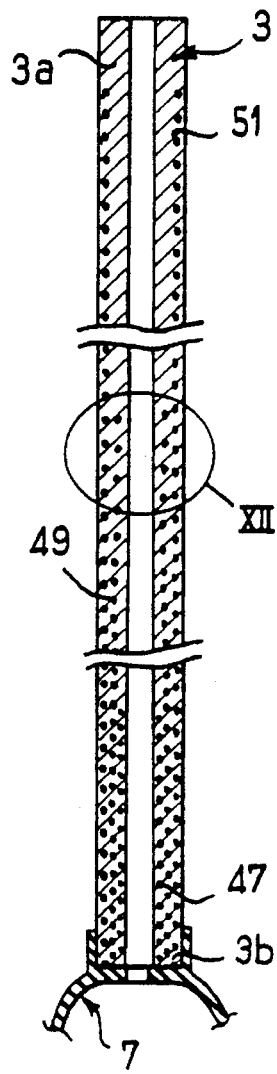
FIG_11
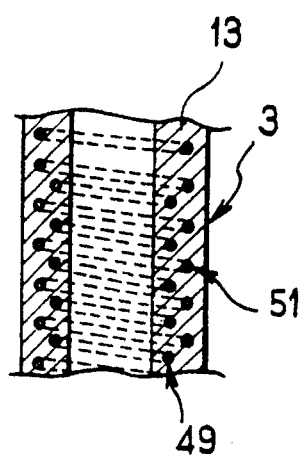
FIG_12
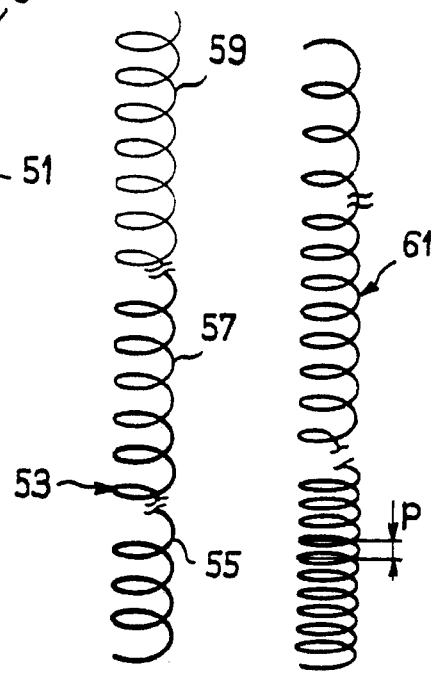
FIG_13  FIG_14

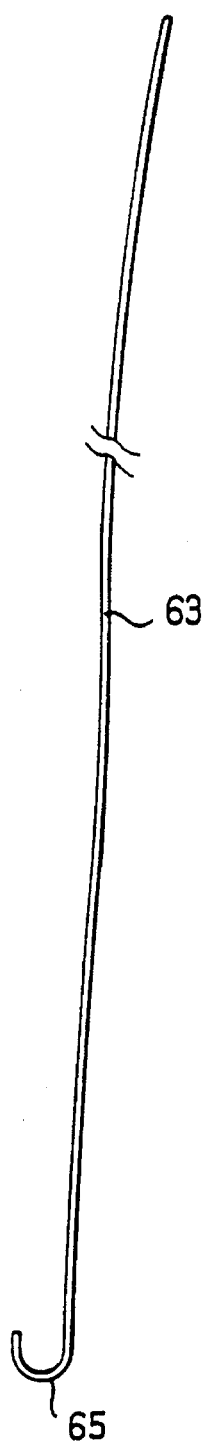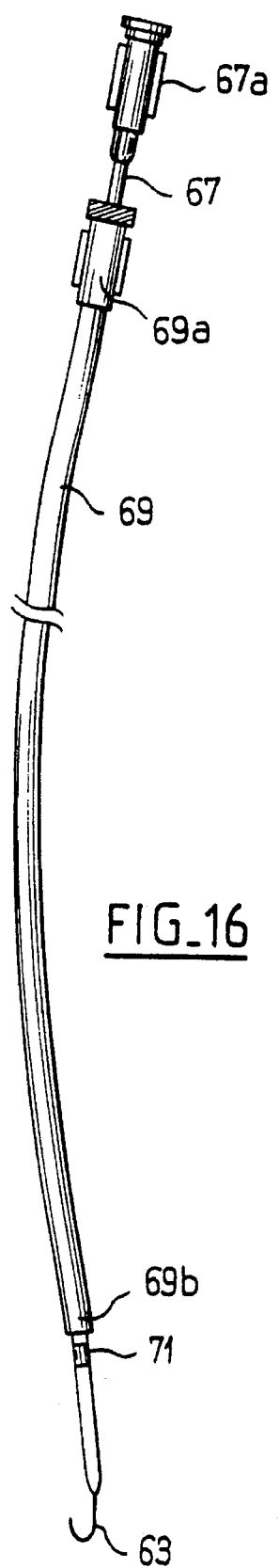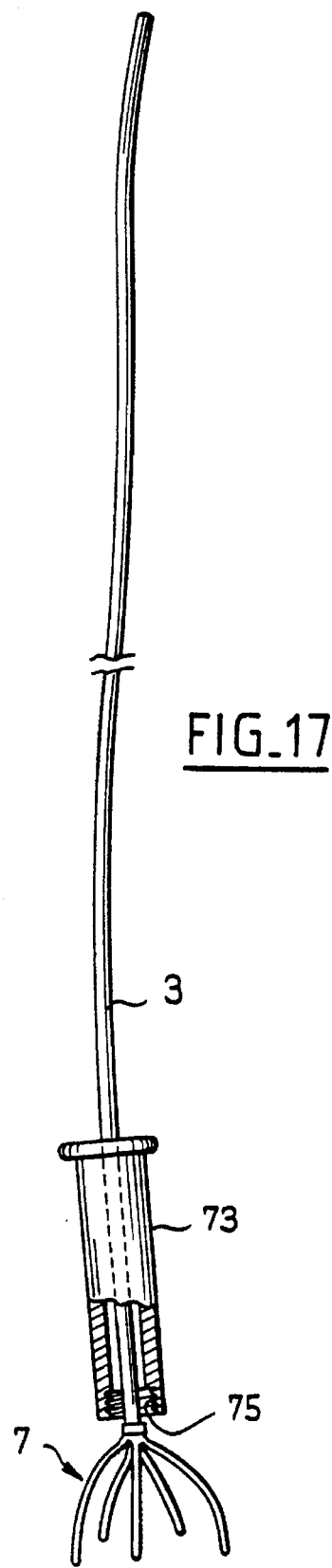
FIG. 15
FIG. 16
FIG. 17

BLOOD FILTERING DEVICE HAVING A CATHETER WITH LONGITUDINALLY VARIABLE RIGIDITY

The invention relates to the area of blood filtration units or devices.

More precisely, within this area, the invention relates to devices which can be implanted in a patient's body and comprises a blood filter which can be positioned in a vessel, at the end of a catheter or a filament extending along the access route followed by the filter to the area where it is to be implanted in the vessel.

This type of device is frequently known as "a temporary filter" since it is more particulary used within the context of vascular treatments which only require the filter to be present for a period restricted a priori in time, frequently of the order of a few days to a few months, for example within the context of the treatment of a thrombus, it being noted, however, that the retention of the device over a longer term can be envisaged, for example within the context of an anti-coagulant treatment.

Whatever the case, one of the advantages of this type of filtration unit is that, as the filter normally does not have any means for definitively attaching it to the wall of the vessel where it is to be installed, the practitioner can remove it when desired, using its transporter catheter for this purpose.

Examples of the production and use of filtration units of this type are described in particular in patents FR-A-2 580 504 and FR-A-2 643 250.

The devices described in these two documents are particularly advantageous in that they propose using as a means of connecting the filter "to the exterior" a catheter which is open over its entire length and at its two opposite ends if necessary, utilising its inner duct for injecting a treatment product towards the filter implantation area, the filter being designed to be secured to the catheter such that it does not block said inner duct thereof.

However, as far as the applicants are aware, account has not hitherto been taken of a problem which can prove to be important in particular with this type of device, namely the migration of the filter.

If, for a circulation of a liquid, or at least for holding the filter, a catheter is used and this catheter is made of a flexible material which helps it to slide along the access route to the vessel, looping effects can appear over its length, which risks moving the unit progressively towards the heart, with the obvious inherent risks. If, on the other hand, the catheter used is more rigid and therefore normally no longer tends to roll up in loops, in contrast, there is a risk of its attenuating or even assisting the thrust which the filter tends to exert thereon, the catheter then tending to pull on the tissues, which is unfavourable for the patient and can lead to additional complications.

It is in particular to overcome these migration problems that the invention proposes a device which can be implanted in a patient's body as far as a blood vessel in order to retain any clots there, this device comprising:

a catheter (or any equivalent elongated blood filter holding mean) having an axis and a length in the direction of the axis, with a proximal end and an opposite distal end;

a blood filter secured to the distal end of the catheter;

the device being characterised in that the catheter used is stiffened in a variable manner over its length so as to be stiffer at its distal end than at its proximal end.

Furthermore, in order, preferably, to enable a liquid or a treatment product possibly to be injected into the filter implantation area (or even a possible blood tap), this variable rigidity can be brought about by progressive longitudinal stiffening of the catheter wall, externally of its internal duct which is thus kept free for the passage of said liquid, in one direction or the other.

In addition to simple and reliable distribution of a treatment product, a catheter of this type with variable rigidity offers a further advantage if it is effectively open.

Given that it represents an advantageous solution to the problem of the possible migration of the filter, it will allow an implantable means for distributing said product to be positioned subcutaneously.

Thus, the risks of infection from the surrounding environment during the implantation period are to a large extent restricted, the entire filtration unit being protected at least by the cutaneous surface of the patient, the treatment product being injected at the suitable moment through the skin and, via said unit, to the area in which the filter is implanted in the vessel.

Preferably, a capsule, which can in particular comprise an inner chamber for accommodating the treatment product and closed by a self-closing wall, which can be perforated by the needle of a syringe for injecting said product through the patient's skin, can be used as the implantable distribution means.

To return briefly to the variable stiffening of the catheter, it will be noted that this stiffening can be achieved in particular in two ways: by internal stiffening of the very wall of this catheter without added auxiliary means (for example, by varying the thickness of this wall or by using telescopic portions), a further solution being to use auxiliary stiffening means which can in particular be embedded in the catheter wall in question.

Advantageously, and in order to obtain the best effect with respect to the retention of the filter, the rigidity of the catheter wall preferably decreases progressively to a greater or lesser extent from its distal end to its proximal end.

For whatever purpose it may serve, it will be noted that the "distal" end of the device designates the end to which the blood filter is secured and which is thus, with this filter, implanted most deeply in the vessel to be filtered, the "proximal" end evidently being the opposite end located closest the surface of the skin, in the vicinity of the outlet of the access route leading to the vessel in question.

Further characteristics and advantages of the invention will appear from the following description given with reference to the attached drawings, in which:

FIG. 1 is a schematic overall view of a detachable blood filtration unit equipped with an implantable chamber;

FIG. 2 is a median view in section of the detail marked II in FIG. 1;

FIG. 3 shows an internal view of the implantable chamber and the manner in which it can be used;

FIG. 4 is a partial view in longitudinal section of the catheter with variable rigidity equipped with the filter according to a first embodiment;

FIG. 5 shows a schematic perspective view of an alternative embodiment of the catheter equipped with the filter;

FIG. 6 shows, in a view similar to FIG. 5, a further alternative embodiment of the catheter with its filter;

FIG. 7 shows the stiffening means used in the embodiment in FIG. 6;

FIGS. 8, 9 and 10 are three views in section along the lines VIII—VIII, IX—IX and X—X respectively in FIG. 6;

FIG. 11 shows in longitudinal section a fourth alternative embodiment of the catheter;

FIG. 12 is an enlarged view of the detail marked as XII in FIG. 11;

FIGS. 13 and 14 show two further possibilities of the variable stiffening of the catheter, here using a helical spring having either a thickness which decreases (FIG. 13) or a widening pitch); and FIGS. 15, 16 and 17 show the principal means used for positioning, or withdrawing, the filtration unit according to the invention.

Since one of the advantages of the use, according to the invention, of a catheter with variable rigidity in conjunction with a blood filter, is thus to permit the use of a chamber which can be implanted under the skin of a patient who is, for example, to undergo thrombolysis, the invention will only be described hereinafter within the context of an application of this type even if it is clear that, if necessary, the proximal end of the catheter may not be connected to a chamber of this type.

FIG. 1 firstly shows, in its entirety, a blood filtration unit 1 which can be positioned percutaneously via the jugular vein.

The unit 1 essentially comprises a sectile catheter 3 with variable rigidity which is connected at its proximal end 3a to an implantable chamber 5, the catheter further being securely connected at its distal end 3b to a blood filter 7.

Since, in accordance with the invention, the internal longitudinal duct 9 of the catheter 3 has to be left free for the passage of the treatment product, such as a medicinal liquid substance used for the lysis of thrombi, it will be seen from FIG. 2 that the filter 7 is secured to the distal end 3b in such a way that the catheter is not blocked (this feature should not, however, be necessarily considered as essential or limiting).

To this end, in the example illustrated, the filter comprises six feet or arms 11 which can expand radially and automatically, so as to constitute a sort of umbrella, such that, in their expanded state (illustrated, for example, in FIG. 1), the arms adopt a substantially conical shape such that via their free ends, which in this case are curved, they can match the corresponding wall of the vessel where the filter is to be implanted, without becoming attached thereto definitively (the feet not having any fastening means at all in the example in question).

Opposite their free ends, the feet of the filter are connected together at an apex or head 14 through the centre of which there passes a passage 15 having a cross-section comparable to that of the duct 9.

Since the filter 7 is normally adapted such that it can be made of metal, for example of steel or cobalt, it can be secured to the catheter by the crimping and/or bonding of its head 14 such that the aperture 15 is in the extension of the conduit 9.

FIG. 3 shows a possible embodiment of the implantable chamber 5.

In this Figure, it can be seen that the chamber in question is in this case formed in the manner of a sealed capsule containing an inner chamber 17 which is closed at the top by a self-closing wall 19 (for example made of silicone plastics material) which can be perforated by the needle 21 of any suitable system, such as syringe, for injecting through the patient's skin, shown schematically at 23.

The base 25 of the capsule can in particular be made of metal, it being possible for the remainder, particularly its lateral wall 27, to be made of electrically insulating material, such as a bio-compatible plastics material.

In order to distribute the product received from the syringe, the space 17 communicates here with the catheter 3 via a conventional union 29.

If, in this construction, the unit 1 is implanted without particular precautions with respect to the rigidity of the catheter 3 being taken, it thus risks coiling up in loops at the location of the heart or, if it is too rigid, exerting a thrusting effect on the chamber, risking transforming the latter into a subcutaneous "tunneller".

To avoid the above occurring, the catheter wall is stiffened such that it is stiffer at the distal end 3b than at its proximal end 3a (where the catheter is thus more flexible), in order to attenuate the thrust effect on the chamber 5. (It will be appreciated that a further solution might consist in stiffening the catheter by introducing a metal cable of variable stiffness, which, for example, might have a diameter which is larger at its distal end than at its proximal end, into its duct 9).

FIGS. 4 to 13 show (within the context of stiffening the wall outside the inner duct) various ways of stiffening the catheter, namely in this case either by structural stiffening of the wall itself, without added auxiliary means (FIGS. 4 and 5), or by using added stiffening means which are connected to this wall and can, in particular, be embedded therein (solutions shown in FIGS. 6 to 14).

In FIG. 4 firstly, the solution used consists in producing the catheter 3 in a plurality of portions, in this case three 31, 33, 35 connected end-to-end coaxially, for example by bonding or welding, each tube portion being produced from a different material having its own degree of rigidity.

The difference in rigidity between the portions 31, 33, 35 can be obtained as a result of polyolefins (such as polyethylene) of high, average and/or low density, or even sequenced polymers (such as A-B) of which one sequence is more rigid than the other and is variable (for example polyether block amide: PEBA), being proportioned or cut to varying proportions.

A further solution, illustrated in FIG. 5, consists in providing a catheter of which the wall thickness decreases from the distal end 3b to the proximal end 3a.

In the embodiment illustrated, this variation in thickness has been produced by the use of three tubes 37, 39, 41 of different lengths and different cross-sections (both internal and external), such that a telescopic assembly is obtained, the tube with the largest cross-section and the shortest length 41 being secured to the filter 7 and accommodating tightly the second tube 39 with a smaller cross-section and a longer length inside which is fitted the third tube 37 with an even smaller cross-section and, a greater length.

If necessary, the last tube 37 can extend to the distal end of the shortest section 41, such that the cross-section of the inner duct 9 of the catheter is constant over its entire length, it being possible for the thickness of each of the tubes 37, 39, 41 to be identical.

In FIG. 6, the variable stiffening of the catheter 3 is brought about by means of added auxiliary means, the catheter itself consisting of a single piece of flexible biocompatible plastics material having a wall thickness which is constant from one end to the other.

Stiffening is brought about by the use of fine filaments or metal rods shown at 43 in FIG. 7, these filaments having to be positioned in passages of suitable cross-section 45, provided in the wall 13 of the catheter surrounding its inner duct 9, these passages, and thus the rods, extending substantially from the distal end 3b in the direction of the proximal end 3a.

In order to vary this rigidity, the use of rods 43 of different lengths can be provided.

In the version illustrated, there are thus provided at the distal end 3b eight channels 45 each enclosing tightly a rod 43 over approximately one third of the length of the catheter (FIG. 8), the second, intermediate third only comprising four channels and four rods (FIG. 9), and the final third extending to the proximal end 3a only enclosing two channels 45 each with a rod 43 (FIG. 10).

Although a priori it appears more simple to provide for the channels to extend substantially parallel to the general longitudinal axis 3c of the catheter and of its internal duct, it is evidently also possible to imagine a helical arrangement.

In the version illustrated in FIG. 11, a plurality of helical springs embedded inside the catheter wall, here consisting of single part of conventional bio-compatible plastics material having a constant thickness, is used instead of the metal rods.

In the version illustrated, there are three portions of helical springs 47, 49, 51 of different lengths disposed coaxially about one another and thus embedded in the wall 13 such that, for example, the outermost spring 51 extends substantially to the vicinity of the two ends of the catheter, the intermediate spring 49 only extending over two thirds of the length from the distal end, the third, innermost spring 47 only extending over the lower third, from this same distal end.

For greater clarity, FIG. 12 shows, in an enlarged view, a detail of the catheter showing the relative arrangement of the longest helical spring 51 and the medium length helical spring 49.

As FIGS. 13 and 14 show respectively, it would also be possible to use only a single helical spring, still embedded in the thickness of the catheter wall but which may comprise a pitch between turns and/or have a variable thickness.

Thus, FIG. 13 shows a helical spring 53 consisting of three metal portions welded end-to-end, namely a first portion 55 with a relatively large thickness (a few tenths of a millimetre), then a second portion 57 with a reduced thickness, itself connected to a third portion 59 with an even smaller section.

With respect to FIG. 14, the helical spring 61 illustrated there has a pitch "p" between turns which increases in one direction.

It will be appreciated that it is either the thickest portion of the spring or the portion having the closest pitch which is disposed at the distal end of the catheter.

With reference to FIGS. 15, 16 and 17, one possible method of implanting the filtration unit 1 will now be described, this implantation being performed under, at least local, anaesthetic.

Firstly, the operator can commence by making in the neck a percutaneous access route to the jugular vein, the filter in this case being implanted in the inferior vena cava (it will be noted that access could also be provided by denuding).

Once this has been performed, the operator firstly introduces a metal guide wire marked 63 in FIG. 15 and having a curved end 65 via the access route provided (jugular vein, then superior vena cava and finally interior vena cava), the cable 63 being inserted until the end 65 is slightly downstream of the filter implantation area.

When the aperture in the access route through the skin has been slightly enlarged, the operator then fits onto the proximal end of the wire 63 (which then emerges from the jugular vein), an assembly consisting of a relatively rigid mandrel 67 and an outer sheathing 69, made of bio-compatible material, the respective proximal ends 67a, 69a of the mandrel and of the outer sheathing then abutting one another.

The operator then gently lowers this assembly along the cable 63 until the radio-opaque mark 71 provided on the mandrel reaches the area provided for the implantation of the filter.

The operator can then withdraw the wire 63, which is nevertheless flexible, and the mandrel 67 surrounding the latter from the sheathing 69.

Once the outer sheathing 69 is thus in position, it is used as a guide for positioning the filter, which is then conventionally pre-arranged in the state in which its feet are radially folded in a sort of packaging syringe 73 open at its two opposite ends so as to enable the catheter 3, which was previously secured to the filter, to be passed through from one side.

Pre-arranged in this way, the body of the syringe 73 is then screwed on at its threaded end 75 to a complementary thread provided on the proximal end piece 69a of the sheathing 69, this operation, evidently, being performed externally of the patient's body.

The operator then lowers into the sheathing the filter followed by its catheter until said filter (still in its retracted state) reaches the distal end 69b of the sheathing where it then naturally expands, taking account of its structure which is compact here, its feet naturally unfolding owing to their flexibility whilst bearing against the inner wall of the vena cava at the desired location.

It will be noted that, in view of the relative rigidity of its wall, the catheter should be able to slide inside the sheathing 69 without necessarily requiring for this purpose the addition of an auxiliary stiffening device, such as a very fine mandrel or detachable metal filament which is frequently slid into highly flexible catheters to facilitate their positioning. If a mandrel of this type is to be provided, it is selected a priori such that it is relatively short and the device is arranged such that, at the end of its travel, it abuts the proximal end of the catheter.

At all events, once the filter/catheter assembly is in place, the operator can then remove the sheathing 69 from the vein.

In now remains for the operator to connect correctly the proximal end of the catheter to the injection means used.

If these means consist of a chamber 5, the operator firstly provides a subcutaneous housing. Once this has been performed, the catheter 3 is cut to a suitable length. The operator fits the capsule 5 to the free cut end, via the union 29, then conceals the assembly in the housing, subsequently closing off the access route in such a way that the capsule is trapped under the skin after suturing, as illustrated in FIG. 3.

By way of indication it will be noted that the mandrel 67 and the sheathing 69 can have a length of the order of 50 to 60 cm, the length of the catheter may be 60 to 80 cm, the cable 63 preferably being slightly longer with a diameter which may be of the order of 0.5 mm, the diameters of the mandrel 67 and of the sheathing being, respectively, of the order of 3 and 4 mm, that of the catheter being slightly less, for example of the order of 2 mm, and its length after cutting possibly being 40 to 50 cm. Especially, if the catheter 3 is not used as a "support" for allowing a fluid circulation therethrough, any equivalent blood filter holding mean could be used, such as a flexible tube or rod, made for example of silicone.

We claim:

1. A device adapted to be implanted in a vessel of a patient's body, for trapping blood clots, said device comprising:

an elongated blood filter holding means comprised of a body having an axis and a length in the direction of said axis, said body also having a proximal end and a distal end; and a blood filter connected to the distal end of said elongated blood filter holding means, stiffening means embedded in the body of said elongated blood filter holding means for stiffening said elongated blood filter holding means in a longitudinally variable manner over its length, wherein said stiffening means are stiffer towards the distal end of the holding means than towards the proximal end for attenuating a substantially axial force exerted on said blood filter when the device is implanted.

2. A device according to claim 1 wherein the stiffness of the stiffening means increases in portions, in a plurality of longitudinal locations, from the proximal end to the distal end of the holding means.

3. A device according to claim 1 wherein the elongated blood filter holding means comprises a catheter and wherein the device further comprises a capsule adapted to be implanted under the patient's skin, said capsule comprising an inner chamber for receiving a treatment product, said chamber being in communication with said proximal end of the catheter at a first end, and being closed by a wall adapted to be perforated by a needle of a syringe for injecting said product through the patient's skin, at a second end.

4. A device adapted to be implanted in a vessel of a patient's body, to trap blood clots, said device comprising:

a catheter having an axis and a length in the direction of said axis, said catheter having a wall a proximal end and a distal end;

said catheter including stiffening means which are stiffer towards the distal end of the catheter than towards its proximal end, for less stiffening of said catheter towards its proximal end than towards its distal end;

a blood filter secured at the distal end of the catheter; and a capsule adapted to be implanted under the patient's skin, said capsule comprising
a housing defining an injection chamber, the housing including a self-closing wall, and
a capsule exit communicating with said inner chamber and passing through said housing, said capsule exit being connected to the proximal end of the catheter.

5. A device according to claim 4 wherein said stiffening means comprises a plurality of rods of various stiffness inside said catheter wall substantially parallel to the axis of the catheter, the number of rods being greater towards said distal end of the catheter than towards the proximal end.

6. A device adapted to be implanted in a vessel of a patient's body, in order to trap any blood clots there, said device comprising:

a catheter having an axis and a length in the direction of said axis, with a proximal end and an opposite distal end, and a blood filter secured at the distal end of the catheter said catheter having a wall and an axial inner duct surrounded by said wall, said catheter having varying degrees of stiffness over its length such that it is stiffer towards its distal end than towards its proximal end for attenuating a substantially axial force exerted on said blood filter when said device is implanted, said stiffening accomplished in a longitudinally variable manner by stiffening said wall to different degrees depending on the location therealong with a plurality of spring means of various rigidity embedded in the thickness of the catheter wall.

7. A device according to claim 6 wherein said spring means comprise helical springs of different lengths, disposed about one another and coaxially to said catheter.

8. A device adapted to be implanted in a vessel of a patient's body for treating a medical affection of said vessel, said device comprising:

a catheter having an axis and a length in the direction of said axis, said catheter having longitudinally opposite proximal and distal ends, and comprising between said ends, a catheter wall surrounding an axial inner duct; and a plurality of spring means of various stiffness embedded in the catheter wall for stiffening said catheter in a longitudinally variable manner, so the stiffness of the catheter is less towards the proximal end thereof than towards the distal end.

* * * * *